's Patent Number: 4,823,789
Date of Patent: Apr. 25, 1989

[54] NOSE TUBE ANCHORING STRIP

[75] Inventor: Arthur A. Beisang, III, Des Moines, Iowa

[73] Assignee: Genetic Laboratories, Inc., St. Paul, Minn.

[21] Appl. No.: 155,819

[22] Filed: Feb. 16, 1988

[51] Int. Cl.⁴ .............................................. A61M 15/08
[52] U.S. Cl. .............................. 128/207.18; 128/911; 128/DIG. 26; 128/171
[58] Field of Search ....... 128/912, 149, 171, DIG. 26, 128/200.26, 207.13, 207.18

[56] References Cited

U.S. PATENT DOCUMENTS

| 3,046,989 | 7/1968 | Hill | 128/DIG. 26 |
| 4,114,626 | 9/1978 | Beran | 128/DIG. 26 |
| 4,120,304 | 10/1978 | Moor | 128/DIG. 26 |
| 4,655,209 | 4/1987 | Scott | 128/156 |
| 4,706,662 | 11/1987 | Thompson | 128/156 |

Primary Examiner—Paul T. Sewell
Assistant Examiner—Kimberly L. Asher
Attorney, Agent, or Firm—Orrin M. Haugen; Thomas J. Nikolai; Frederick W. Niebuhr

[57] ABSTRACT

An adhesive coated sheet particularly shaped to facilitate the anchoring of a nasal-gastric tube to the nose of a patient to prevent accidental dislodgment thereof.

7 Claims, 1 Drawing Sheet

NOSE TUBE ANCHORING STRIP

BACKGROUND OF THE INVENTION

I. Field of the Invention

This invention relates generally to a disposable device for anchoring a nasal-gastric tube in place on the body of a patient and more particularly to a prefabricated adhesive appliance especially shaped to facilitate its attachment to a nasal-gastric tube and to the patient's nose.

II. Discussion of the Prior Art

During the course of certain medical procedures, it is necessary to intubate a patient with a nasal-gastric tube which is routed through the patient's nasal passage through the pharynx and esophagus and into the stomach. It is important that this tube be anchored so that it will not be allowed to move appreciably following intubation. Such movement could result in damage to delicate tissues lining the nasal and digestive tract or may cause it to move out of position, rendering it non-functional.

The practice in the past for immobilizing a nasal-gastric tube has been to use adhesive tape cut from a roll to effectively strap down the tube by taping it to the patient's face off to one side of the nose and upper lip. The number of strips of tape and the manner of application was left to the best judgment of the medical attendant.

The above-described prior art method is less than satisfactory from a number of standpoints. First of all, the custom cutting, placement and taping down of the tube tends to be time-consuming. Secondly, the tape commonly used is formulated with water-based adhesives which lose their adhesive ability after being wetted by body fluids and secretions, thus requiring multiple retaping operations while the tube is in place. Thirdly, and more important, when the nasal-gastric tube is pulled to one side and taped down, the tube applies pressure to the tissue surfaces surrounding the nasal opening which, after a short time, commonly results in pain and discomfort for the patient. If not properly attended to, this area of the nose will become irritated to the point where an open sore can result.

So that a low friction coefficient will exist between the outer surface of the tube and the delicate tissues which it engages, such tubes are often fabricated from silicon plastic or, alternatively, are coated with a hydrophilic material. These materials thus tend to exhibit a non-stick surface which allows "tromboning" to take place. That is, the tube tends to slip back and forth relative to the custom taping. As mentioned, to prevent irritation to delicate tissues, this movement must be substantially eliminated.

A final drawback to the prior art method and means for anchoring a nasal tube by custom taping is that it tends to be unsightly where numerous strips of tape are made to crisscross over the patient's face.

SUMMARY OF THE INVENTION

In accordance with the present invention, there is provided a prefabricated adhesive or strip patch which is preshaped to facilitate its attachment to a nasal-gastric tube and to the nose surface of a patient and which is, therefore, substantially easier to use and apply than earlier custom taping methods. The device comprises a thin plastic backing material of a type exhibiting uniaxial stretch properties, permeability to moisture and air and which exhibits a compliance modulus irrespective of thickness in the range of from 0.5 to 110 pounds per inch, along with an elastic recovery which is less than 98%. The tube anchoring device of the present invention is precut so as to have an inverted T-shaped tube engaging zone integrally joined to a nose engaging zone. The stem portion of the inverted T-shape zone extends along the easy stretch axis of the material and the cross portion of the T-shape zone extends transverse to that easy stretch axis. The nose engaging zone has a curved or arcuate edge extending normally to the easy stretch direction and a pair of oblique edges joined to the end of the stem of the inverted T. This shape, when applied, lies flat against the end portion of the nose below its bridge, conforming to contours of the nose.

The patch of flexible plastic backing material then has a layer of a biocompatible pressure-sensitive adhesive co-extensive with one major surface thereof and, when packaged, will have a protective layer of release paper adhered to the adhesive coating.

In use, after the nasal tube has been inserted into the nose and digestive tract of the patient, the device is removed from its sterile envelope. Portion of the release paper covering the nose engaging zone are removed. The nose engaging portion of the patch is then formed around the outer surface of the nose below its bridge. Next, the release paper is removed from the inverted T-shaped zone and the tube to be anchored is aligned with the stem of the "T" while the cross-portion of the "T" is wrapped around the outer cylindrical surface of the tube just below the tip of the nose.

Because of the above-described physical properties of the backing material, the anchoring device exhibits "dynamic adhesion", meaning that it has stretch properties similar to that of skin and can move with movement of the skin so as to inhibit it from wrinkling and coming loose from the skin surface. Moreover, the nasal tube is personally aligned with the easy stretch axis of the material, allowing limited floatation of the nasal tube within the nasal opening and eliminating unwanted pressure between the tube surface and the nose tissues.

Using the present invention, a nasal gastric tube can be anchored in a matter of moments, with the anchor being neat in appearance and effective in use.

OBJECTS

It is accordingly a principal object of the invention to provide an improved means for anchoring a nasal tube on a patient.

Another object of the invention is to provide a preformed nasal tube anchoring device which can be applied in only a few seconds and which can be left in place for prolonged periods without causing irritation to skin tissues of the nose.

Still another object of the invention is to provide an anchoring device for securing a length of medical tubing to the body of a patient comprising a preshaped adhesive patch which, because of its shape, readily conforms to the surfaces to which attachment is to be made.

A further object is to provide a device to securely anchor a tube to the body at locations that are exposed to body fluids and/or water.

These and other objects and advantages of the invention will become apparent to those skilled in the art from the following detailed description of a preferred embodiment, especially when considered in conjunction with the accompanying drawings.

DESCRIPTION OF THE PREFERRED EMBODIMENT

Figures 1, 2:
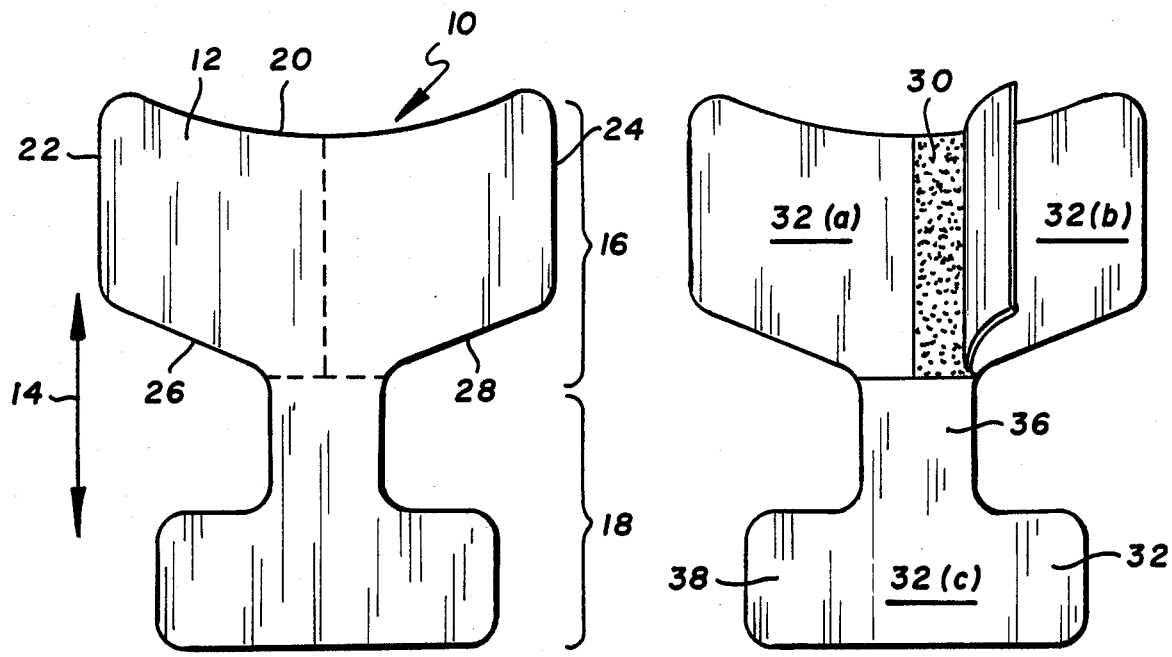
FIG. 1 is a top view of the tube anchoring device when laid flat.
FIG. 2 is a bottom view of the tube anchoring device of the present invention.

In accordance with the present invention, the preformed nasal tube anchoring device 10 is seen to comprise a thin film sheet of plastic backing material 12 which is preferably formed from either a woven or nonwoven polymeric material having a pattern of fibers oriented therein so that the film material exhibits a preferred or easy direction of stretch indicated by the arrow 14.

The plastic material 12 is also of a type that is pervious to moisture and air which allows the area beneath it when it is applied to the skin to "breathe". When converting the large sheets of plastic backing material in a rotary die-cutting operation, it is possible to cut the material on a bias, i.e., at a predetermined angle to the easy stretch axis 14, thereby yielding a product exhibiting a desired compliance modulus and a desired elastic recovery. It has been found that a compliance modulus irrespective of thickness in the range of from 0.5 to 110 pounds per inch and an elastic recovery factor less than 98% yields excellent results in that the resulting product is found to exhibit stretch characteristics corresponding closely to that of skin. Thus, when the backing sheet 12 is adhesively bonded to the skin, the anchoring device will flex with skin movement, thereby avoiding puckering and disattachment of the anchor.

With continued reference to FIG. 1, the anchoring device can be thought of as being effectively divided into two zones, namely, a nose engaging zone identified by brackets 16 and a tube engaging zone identified by brackets 18. The tube engaging zone 18 has the shape of an inverted T and is integrally joined with the nose engaging zone 16 along the end of the stem portion thereof. The nose engaging zone has an arcuate edge 20 extending generally transverse to the direction of the easy stretch axis identified by arrow 14 along with opposed side edges 22 and 24 extending generally parallel to the easy stretch axis. The edges 22 and 24 then join to the stem of the T by obliquely directed edges 26 and 28.

Referring to FIG. 2, it can be seen that the plastic backing sheet 12 is coated over its entire back surface with an adhesive layer 30. The adhesive employed may be any one of a number of bio-compatible, non-allergenic adhesives, examples of which include polymethacrylate, polyvinyl ethyl ether, polyacrylate and acrylic ester copolymer. These adhesives have been used in the past with various forms of bandages and wound dressings and exhibit good adhesion properties even to so-called non-stick surfaces, such as Teflon plastic and hydrophylic coatings. Also, they are substantially non-irritating to dermal tissues and do not deteriorate when exposed to water and/or body fluids.

To protect the adhesive layer 30 prior to use, that layer is preferably covered with a layer of release paper 32 which may be readily peeled off prior to use to expose the adhesive layer. To facilitate applying the nose anchor of the present invention, the release paper layer 32 is preferably segmented into three parts labeled 32(a), 32(b) and 32(c). Various types of release papers are known in the art and which are compatible with the above-identified adhesive materials.

Figure 3:
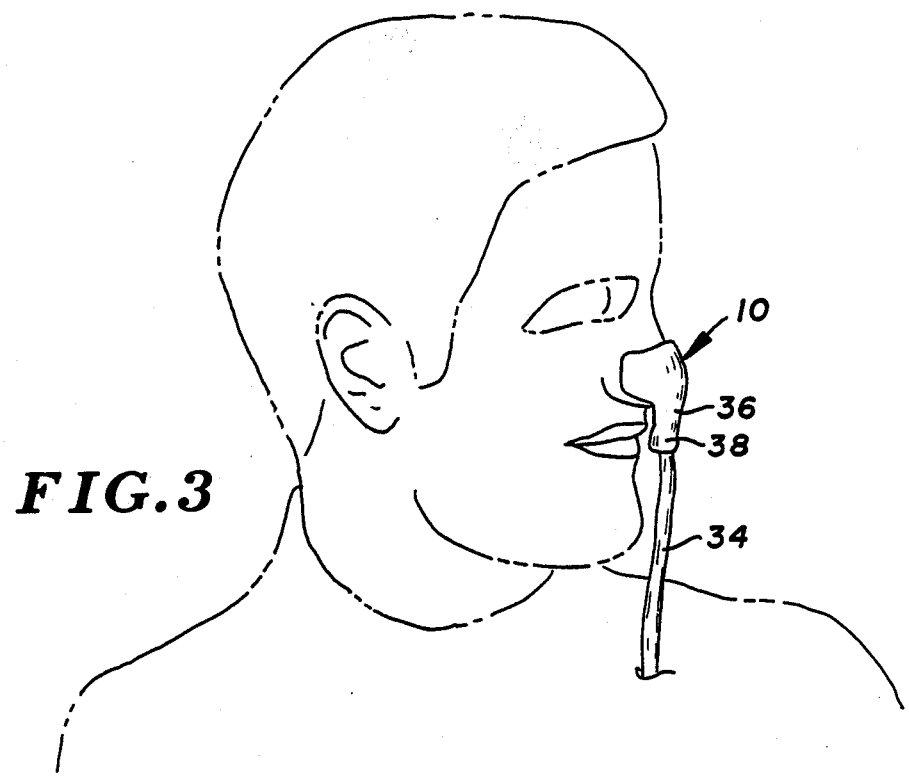
FIG. 3 is a side view showing the manner in which the tube anchoring device of the present invention is applied to the patient.

With reference to FIG. 3, when using the nasal tube anchor of the present invention, once the flexible plastic tube 34 has been routed through the patient's nasal opening and through the pharynx and esophagus into the stomach, the medical attendant will remove the anchor device 10 from its sterilized envelope (not shown) and will peel off one of the release paper segments 32(a) or 32(b) and will affix the underlying portion to one side of the nose surface proximate the tip thereof and then will remove the other release paper section 32(a) or 32(b) and press the exposed adhesive layer against the other side surface of the nose tip. By proceeding in this fashion, the likelihood of adhering the adhesive layer to itself is minimized. Once the nose engaging zone 16 of the anchor has been attached to the surface of the nose, the medical attendant will next remove the release paper segment 32(c) and while grasping the tube 34, will form the stem portion 36 of the inverted T-shaped zone about the outer surface of the tube 34 while wrapping the cross portion 38 of the T-shaped zone completely around the outer surface of the tube 34.

Because of the unidirectional stretch properties of the anchor device 10, the tube 34 tends to float within the nasal opening rather than being forced against the skin tissue as with the prior art custom anchoring technique. As such, the likelihood of occurrence of pressure sores is markedly reduced.

In an experiment conducted with nose anchors made in accordance with the above-described preferred embodiment, it was possible to suspend a 7 pound weight from the tube 20 without destroying the integrity of the anchoring device 10. Nonetheless, the patch could be easily removed from the nose tissue. Less than 30 seconds is required to complete the entire anchoring operation and, when completed, the patient's face is not covered with a mass of unsightly adhesive tape.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can he accomplished without departing from the scope of the invention itself.

What is claimed is:

1. A device for anchoring a gastro-intestinal tube to the nose of a patient, comprising:

a planar sheet of flexible plastic material exhibiting a uniaxial stretch property along an easy stretch axis and a compliance modulus irrespective of thickness in the range of from 0.5 to 110 pounds per inch and an elastic recovery less than 98%, said sheet being bilaterally symmetrical and including a concave, arcuate, upper edge extending generally transverse to said easy stretch axis and first and second notches downwardly displaced from said upper edge with one edge of each of said notches being inwardly and downwardly sloping and the notches extending inwardly toward the center of said sheet from the opposed side edges of said sheet to define therebetween a medial strip of a predetermined length and width dimension corresponding to the outer diameter of the tube to be anchored, said medial strip being aligned with said easy stretch axis, said planar sheet being coated on one major surface thereof with a biocompatible adhesive material.

2. The device as in claim 1 and further including a removable backing sheet of release paper adhered to said adhesive coating.

3. A device for anchoring a length of medical tubing in the nose of a patient comprising:
(a) a planar sheet of flexible plastic material which is bilaterally symmetrical and exhibits a uniaxial stretch property along an easy stretch axis and a compliance modulus irrespective of thickness in the range of from 0.5 to 110 pounds per inch and an elastic recovery less than 98%, said sheet including a generally T-shaped tube engaging zone integrally joined to a nose engaging zone where the stem portion of said T-shaped zone is medially aligned with said nose engaging zone and extends along said easy stretch axis and the cross portion of said T-shaped zone extends transverse to said easy stretch axis, said nose engaging zone including an upper concave edge extending transverse to said easy stretch axis and a lower edge sloping downwardly and inwardly from the opposed side edges of said nose engaging zone to meet with said stem portion of said T-shaped zone; and
(b) a layer of non-allergenic, pressure-sensitive adhesive adhered to said planar sheet on one major surface thereof.

4. The device as in claim 3 and further including a layer of release paper adhered to said adhesive layer and coextensive therewith.

5. The device as in claim 4 wherein said layer of release paper is divided into plural segments, one segment being coextensive with said T-shaped tube engaging zone and two additional segments being co-extensive with said nose engaging zone.

6. The device as in claim 3 wherein said plastic sheet comprises a nonwoven polymeric material pervious to air and moisture.

7. The device as in claim 3 wherein said non-allergenic adhesive is selected from a class including polymethacrylate, polyvinyl ethyl ether, polyacrylate and acrylic ester copolymer.

* * * * *